(12) United States Patent
Antwiler et al.

(10) Patent No.: US 7,201,848 B2
(45) Date of Patent: Apr. 10, 2007

(54) METHODS AND APPARATUS FOR SEPARATION OF PARTICLES

(75) Inventors: Glen Delbert Antwiler, Lakewood, CO (US); Linda A. Taylor, Littleton, CO (US)

(73) Assignee: Gambro BCT, Inc., Lakewood, CO (US)

( * ) Notice: Subject to any disclaimer, the term of this patent is extended or adjusted under 35 U.S.C. 154(b) by 158 days.

(21) Appl. No.: 10/310,528

(22) Filed: Dec. 4, 2002

(65) Prior Publication Data

US 2003/0116512 A1 Jun. 26, 2003

Related U.S. Application Data

(60) Provisional application No. 60/338,938, filed on Dec. 5, 2001.

(51) Int. Cl.
*B04B 3/00* (2006.01)
*B04B 11/04* (2006.01)
*B04B 7/16* (2006.01)
*B01D 21/26* (2006.01)
*B04B 11/00* (2006.01)
*B04B 7/00* (2006.01)

(52) U.S. Cl. .................. 210/782; 210/252; 210/259; 210/512.1; 210/257.1; 210/786; 210/787; 210/789; 210/806; 435/2; 494/17; 494/20; 494/37; 494/43

(58) Field of Classification Search ............... 210/252, 210/257.1, 259, 512.1, 782, 786, 787, 789, 210/806; 435/2; 494/16, 17, 20, 37, 43
See application file for complete search history.

(56) References Cited

U.S. PATENT DOCUMENTS 2,616,619 A 11/1952 MacLeod (Continued)

FOREIGN PATENT DOCUMENTS

DE 2545283 A1 4/1977

(Continued)

OTHER PUBLICATIONS

"Centrifugal Elutriation—How it Works", Beckman, pp. 1-7, undated.

(Continued)

*Primary Examiner*—Krishnan S. Menon
(74) *Attorney, Agent, or Firm*—Laura B. Arciniegas; Edna M. O'Connor; John R. Merkling

(57) ABSTRACT

The present invention is directed to a method and system that separates first particles from second particles, or white blood cells from red blood cells, by sedimentation in a fluid chamber with debulking of one of the first or second particles or red blood cells through the inlet of the fluid chamber. The method and system further includes fractionation of the remaining particles or white blood cells into selected subsets. In one embodiment of the instant invention a blood product containing white blood cells is loaded in a separation chamber, a diluting or sedimenting agent is added to encourage rouleaux formation of any red blood cells, the cells are sedimented and the red blood cells are removed.

13 Claims, 5 Drawing Sheets

U.S. PATENT DOCUMENTS

| | | | |
|---|---|---|---|
| 3,825,175 | A | 7/1974 | Sartory |
| 3,987,961 | A | 10/1976 | Sinn et al. |
| 4,091,989 | A | 5/1978 | Schlutz |
| 4,111,199 | A | 9/1978 | Djerassi |
| 4,146,172 | A | 3/1979 | Cullis et al. |
| 4,187,979 | A | 2/1980 | Cullis et al. |
| 4,269,718 | A | 5/1981 | Persidsky |
| 4,322,298 | A | 3/1982 | Persidsky |
| 4,350,283 | A | 9/1982 | Leonian |
| 4,413,772 | A | 11/1983 | Rohde et al. |
| 4,701,267 | A | 10/1987 | Watanabe et al. |
| 4,798,579 | A | 1/1989 | Penhasi |
| 4,808,151 | A | 2/1989 | Dunn, Jr. et al. |
| 5,224,921 | A | 7/1993 | Dennehey et al. |
| 5,362,291 | A | 11/1994 | Williamson, IV |
| 5,370,802 | A | 12/1994 | Brown |
| 5,437,624 | A | 8/1995 | Langley |
| 5,529,691 | A | 6/1996 | Brown |
| 5,549,834 | A | 8/1996 | Brown |
| 5,643,786 | A | 7/1997 | Cohen et al. |
| 5,674,173 | A | 10/1997 | Hlavinka et al. |
| 5,702,357 | A | 12/1997 | Bainbridge et al. |
| 5,722,926 | A | 3/1998 | Hlavinka et al. |
| 5,792,038 | A | 8/1998 | Hlavinka |
| 5,939,319 | A | 8/1999 | Hlavinka et al. |
| 6,051,146 | A | 4/2000 | Green et al. |
| 6,053,856 | A | 4/2000 | Hlavinka |
| 6,334,842 | B1 | 1/2002 | Hlavinka et al. |
| 6,352,499 | B1 * | 3/2002 | Geigle .......................... 494/37 |
| 2002/0114793 | A1 | 8/2002 | Edelson et al. |

FOREIGN PATENT DOCUMENTS

| | | |
|---|---|---|
| DE | 2658926 A1 | 6/1978 |
| WO | WO 92/18222 | 10/1992 |
| WO | WO97/30748 | 8/1997 |
| WO | WO 9818403 A1 * | 5/1998 |

OTHER PUBLICATIONS

"New! Multichamber counterflow centrifugation system", dijkstra vereenigde b.v., undated.

Almici, et al, "Counterflow Centrifugal Elutriation: Present and Future", *Bone Marrow Transplantation,* 1993, 12:2105-8.

AuBuchon, et al, "Cost-Effectiveness of Leukocyte Depletion of Blood Components", presentation at 1993 AABB Meeting, Miami Beach, Florida.

Brown, et al, "Evaluation of a new Separation Method Utilizing Plasma Recirculation and Auto-Elutriation", *Transfusion,* 1994, vol. 34, supplement, Abstract S237.

Faradji, et al, "Large scale isolation of human blood monocytes by continuous flow centrifugation leukapheresis and counterflow centrifugation elutriation for adoptive cellular immunotherapy in cancer patients", *J. of Immunological Methods,* 174, 1994, 297-309.

Figdor, et al, "Isolation of Functionally Different Human Monocytes by Counterflow Centrifugation Elutriation", *Blood,* vol. 60, No. 1, Jul. 1982, pp. 46-52.

Figdor, et al, "Theory and Practice of Centrifugal Elutriation (CE): Factors Influencing the Separation of Human Blood Cells", *Cell Biophysics* 5, 105-1118, 1983.

Gao, et al, "Implementation of a Semiclosed Large Scale Counterflow Centrifugal Elutriation System", *J. of Clinical Apheresis,* 3:1654-160, 1987.

Grabske, Robert J., "Separating Cell Populations by Elutriation", Beckman Instruments, Inc., pp. 1-8.

Griffith, Owen M., "Separation of T and B Cells from Human Peripheral Blood by Centrifugal Elutriation", *Analytical Biochemistry* 87, 97-107, 1978.

Heraeus Sepatech, "Product News, the Curamé3000 elutriation system", undated.

Jemionek et al, "Variations in CCE Protocol for Cell Isolation", *Elutriation,*pp.17-41, undated.

Jemionek, et al, "Special Techniques for the Separation of Hemopoietic Cells", Current Methodology in Experimental Hematology, ed. S.J. Baum, Karger, Basel, chap. 2, pp. 12-16, (1984).

Keng, et al, "Characterization of the Separation Properties of the Beckman Elutriator System", *Cell Biophysics,* 3, 41-56, 1981.

Lindahl, P.E., "On Counter Streaming Centrifugation in the Separation of Cells and Cell Fragments", *Biochemica et Biophysica Acta,* vol. 21, 1950, pp. 411-415.

Loper, K.A., " T-Cell Depletion (TCD) of Peripheral Blood Stem Cell Products (PBSC) Using a Novel Cellular Separation System", Ishage 2001, Poster, Jun. 14-17, 2001.

Noga, et al, "Development of High Capacity Semi-automated Monocyte Isolation System for the Generation of Dendritic Cells (DC)", 43rd ASM Annual Meeting: Abstract #5546777, undated.

Noga, Stephen J., Monocyte Isolation from Peripheral Blood Using a Novel Semi-Automated Cellular Separation System, HSANZ 2001, oral presentation, Oct. 21-24, 2001.

Persidsky, et al, "Separation of Platelet-Rich Plasma by Modified Centrifugal Elutriation", *J. of Clinical Apheresis* 1:18-24, 1982.

Plas et al, "Application News, the Curamé 3000 AN 14". "Isolation of Large Numbers of Highly Purified Lymphocytes and Monocytes by means of the Counterflow Centrifugation Technique in a Curamé 3000", Heraeus Sepatech, undated.

Rouard, et al, Monocyte Purification in a Closed and Single use Device for Dendritic Cell Generation in Clinical Use, undated.

Rouard, et al, A closed and single-use system for monocyte enrichment: potential for dendritic cell generation for clinical applications, pp. 1-18, undated.

Rouard, Helene, "Highly Purified Monocytes for Clinical Application Using the Cobe® Spectra CPS System," HSANZ 2001, oral presentation, Oct. 21-24, 2001.

Sanderson, et al, "Design Prinicples for a Counterflow Centrifugation Cell Separation Chamber", *Analytical Biochemistry,* 71, 615-622, 1976.

Sanderson, Richard J., "Separation of Different Kinds of Nucleated Cells from Blood by Centrifugal Elutriation", *Cell Separation Methods and Selected Applications,* vol. 1, chap. 7, pp. 153-168, undated.

Van Wie, Bernard, et al, "The Effect of Hematocrit and Recycle on Cell Separations", *Plasma Ther Transfus Technol,* 1986, 7:373-388.

Patent Cooperation Treaty International Search Report (PCT/ISA/210) for International Application No. PCT/US02/38566, mailed Aug. 6, 2003.

* cited by examiner

METHODS AND APPARATUS FOR SEPARATION OF PARTICLES

CROSS-REFERENCE TO RELATED APPLICATIONS

This Application claims priority to U.S. provisional application Ser. No. 60/338,938, filed Dec. 5, 2001, which is incorporated herein by reference in its entirety to the extent not inconsistent herewith.

BACKGROUND OF THE INVENTION

1. Field of the Invention

The present invention relates to a system and method for separating particles. The invention has particular advantages in connection with separating white blood cells into desired subsets and debulking red blood cells from such white blood cells.

This application is related to U.S. Pat. No. 6,051,146 issued on Apr. 18, 2000. The entire disclosure of this U.S. patent is incorporated herein by reference to the extent it is not inconsistent.

2. Description of the Related Art

Whole blood consists of a liquid component and particle components. Sometimes, the particle components are referred to as "formed elements". The liquid portion of blood is made up of plasma, and the particle components primarily include red blood cells (erythrocytes) (RBCs), white blood cells (WBCs), and platelets (thrombocytes). While these constituents have similar densities, their average density relationship, in order of decreasing density, is as follows: red blood cells, white blood cells, platelets, and plasma. In addition, the particle constituents are related according to size, in order of decreasing size, as follows: white blood cells, red blood cells, and platelets. The sedimentation velocities of the particle constituents are related to their size and density.

In the medical field it is often desirable to separate blood or blood components. Most current separation devices rely on density and size differences or surface chemistry characteristics to separate and/or filter blood components for transfusion or reinfusion purposes. Typically, blood components are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Although some centrifugal separation techniques are effective at separating some blood components from one another, many centrifugal separation processes are not capable of producing a highly purified end product.

In one type of separation procedure, white blood cells are collected by leukapheresis. Such collection typically uses a centrifuge as described above. The resulting harvested white blood cells can then be further separated into subsets of desired cells for collection if desired. Such subsets of cells desired for collection may include monocytes, lymphocytes, granulocytes, and dendritic cells, although it is understood that collection of other cells may also be desired. The collected leukapheresis products, however, are often contaminated with platelets and red blood cells which can interfere with various cell separation and/or cell selection techniques and later cultivation of the selected cells for therapeutic use.

White blood cells can also be collected by other known methods other than apheresis and again further separated into subsets of desired cells for collection.

Several methods have been proposed for the separation or fractionation of white blood cells from other particles and into selected subsets. One such method is centrifugal elutriation. In one common form of elutriation, a cell batch is introduced into a funnel-shaped chamber located in a spinning centrifuge. A flow of liquid elutriation buffer is then introduced into the chamber having the cell batch. As the flow rate of the liquid buffer solution is increased through the chamber (usually in a stepwise manner), the liquid sweeps smaller sized, slower-sedimenting cells toward an elutriation boundary within the chamber, while larger, faster-sedimenting cells migrate to an area of the chamber where the centrifugal force and the sedimentation (drag) forces are balanced.

Thus, centrifugal elutriation separates particles having different sedimentation velocities. Stoke's law describes sedimentation velocity (SV) of a spherical particle, as follows:

$$SV = \frac{2}{9} \frac{r^2 (\rho_p - \rho_m) g}{\eta}$$

where,
r is the radius of the particle,
$\rho_p$ is the density of the particle,
$\rho_m$ is the density of the liquid medium,
$\eta$ is the viscosity of the medium, and
g is the gravitational or centrifugal acceleration.

Because the radius of a particle is raised to the second power in the Stoke's equation and the density of the particle is not, the size of a cell, rather than its density, greatly influences its sedimentation rate. This explains why larger particles generally remain in a chamber during centrifugal elutriation, while smaller particles are released, if the particles have similar densities.

One problem with purifying white blood cells from other cells and into separate selected subsets utilizing centrifugal elutriation is that the presence of too many red blood cells in the starting white blood cell product can cause non-ideal cell separation as a result of the non-spherical shape of red blood cells and the resulting cell-cell interactions.

Another method of fractionating white blood cells from other particles and into selected subsets is the use of fluidized bed technology as disclosed in U.S. Pat. No. 5,674,173, the disclosure of which is incorporated herein by reference to the extent it is not inconsistent. Again, the presence of too many red blood cells can cause non-ideal cell separation.

To address this problem, white blood cell products in the past have initially been separated from or debulked of red blood cells by density gradient centrifugation, using various separation media. In density gradient centrifugation, a sample is layered on top of a media support and centrifuged. Under centrifugal force, the particles in the sample will sediment through the media in separate zones according to their density.

Many different types of separation media are used in density gradient centrifugation, depending upon the exact application (i.e., Sucrose, CsCl, Ficoll, Hypaque, Percol). Though available commercially, most are not FDA approved and may be deleterious to some human cell populations. The most widely used separation media is perhaps Ficoll-Paque, a solution of Ficoll and sodium diatrizoate. It is formulated to deplete the majority of granulocytes and red blood cells, while retaining a purified fraction of the mononuclear cells (lymphocytes plus monocytes). The disadvantages of using Ficoll-Paque for debulking red blood cells include the loss of 50±15% of the desired cells, and that is not currently used in a closed system.

It is know that red blood cells under proper conditions have the tendency to adhere to each other forming red blood cell rouleaux. Rouleaux formation and size, and therefore red cell sedimentation velocity, is influenced by the hematocrit of the cell suspension, exposure to shear, protein concentration, and presence of sedimentation agents.

It is against this background that the instant invention was conceived.

SUMMARY OF THE INVENTION

It is one aspect of the instant invention to separate or fractionate white blood cells in a separation chamber wherein the chamber can be easily debulked of any red blood cells to facilitate subsequent separation or fractionation.

It is a further aspect of the instant invention to encourage rouleaux of the red blood cells to increase the sedimentation velocity of the red blood cells and enhance their separation from white blood cells.

The present invention is directed to a method and system that substantially obviates one or more of the limitations of the related art. To achieve these and other advantages and in accordance with the purpose of the invention, as embodied and broadly described herein, the invention includes a method of separating white blood cells from red blood cells through sedimentation. In the method, a fluid chamber is rotated about an axis of rotation and a first liquid blood product carrying the white blood cells and red blood cells, as well as any other cells, is passed into the inlet of the fluid chamber. The method further involves sedimenting red blood cells in the fluid chamber and then pulling or debulking the red blood cells out through the inlet of the chamber. The method further includes fractionation of the white blood cells into selected subsets.

In another aspect, the invention includes a method of debulking red blood cells from white blood cells by providing a starting blood product containing at least white blood cells, red blood cells and may contain platelets, loading a separation chamber with the starting blood product, adding a diluting or sedimenting agent to encourage rouleaux formation of the red blood cells, sedimenting the particles and pulling the sedimented red blood cells from the separation chamber.

In a further aspect the invention relates to the method of separation of first particles from second particles by increasing the sedimentation velocity of one of the groups of particles and removing the particles having the increased or higher sedimentation velocity. Apparatus including a system for practicing the methods described above is also contemplated.

An additional aspect of the invention relates to a disposable for a centrifugal separator having a smooth surface wall forming a generally conical shape fluid chamber and a further particle concentrator.

Although the present invention is particularly directed to separating white blood cells into desired selected subsets wherein such white blood cells are collected by leukapheresis, it is understood that the techniques of the present invention can also apply to white blood cells collected using other well known collection methods and from sources other than peripheral blood, including, but not limited to, bone marrow and umbilical cord blood. It is further understood that the desired debulking could be used to separate white blood cells from red blood cells, both with or without the subsequent separation of white blood cells into white blood cell subsets. Also, it is understood that the debulking procedures described could also apply to the separation of other types of cells and to other types of particles. Therefore, both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate an embodiment of the invention and, together with the description, serve to explain the principles of the invention. In the drawings.

DESCRIPTION OF THE PREFERRED EMBODIMENT

Figure 1:
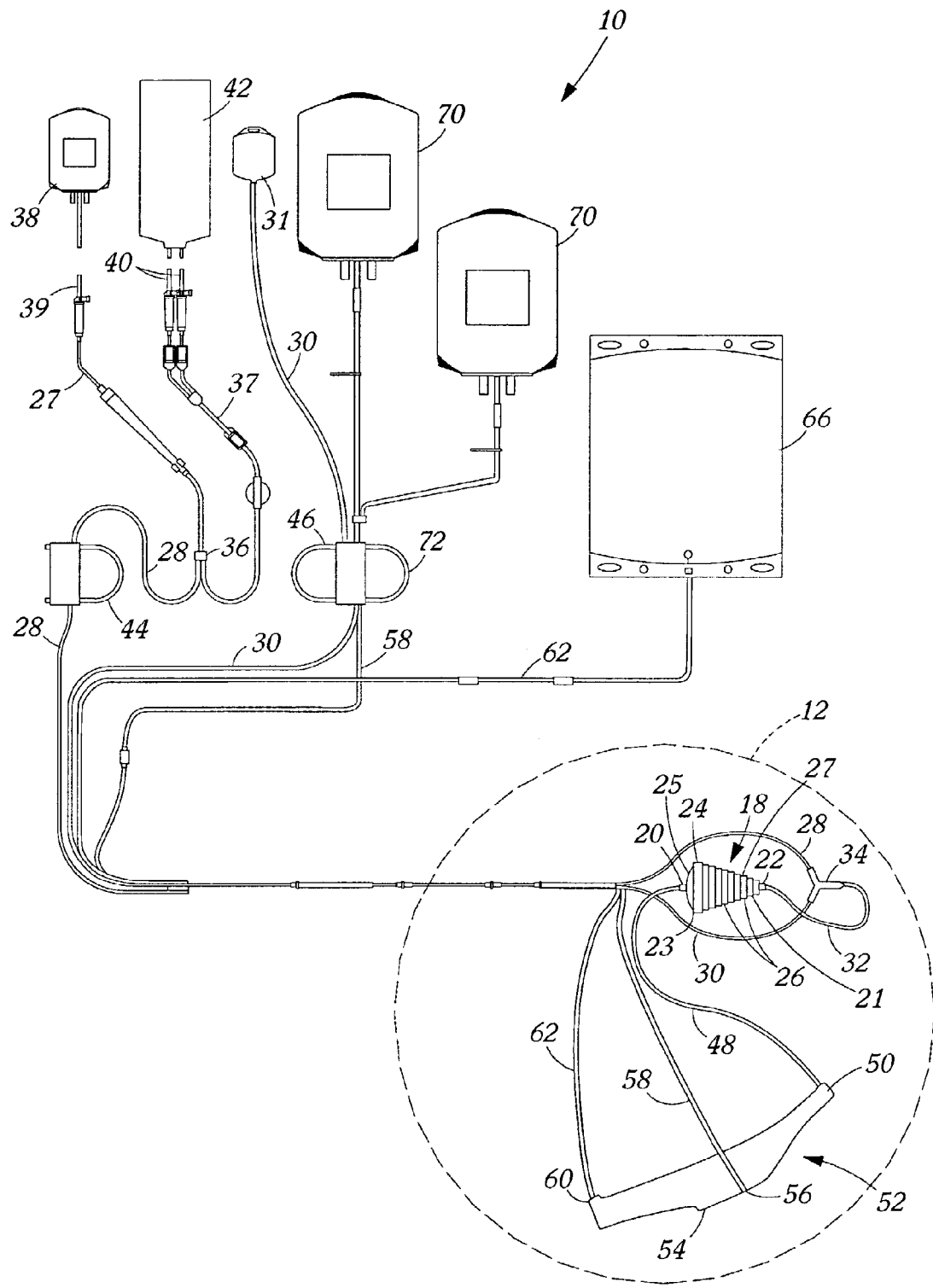
FIG. 1 is a schematic diagram of a particle separation system in accordance with an embodiment of the invention.

Reference will now be made in detail to the embodiments of the invention, examples of which are illustrated in the accompanying drawings. Wherever possible, the same reference numbers are used in the drawings and the description to refer to the same or like parts.

The embodiment of the present invention preferably includes a COBE® SPECTRA™ blood component centrifuge manufactured by Gambro BCT, Inc. of Colorado. The COBE® SPECTRA™ centrifuge incorporates a one-omega/two-omega sealless tubing connection as disclosed in U.S. Pat. No. 4,425,112 to Ito, the entire disclosure of which is incorporated herein by reference. Although the embodiments of the invention are described in combination with the COBE® SPECTRA™ centrifuge, this reference is made for exemplary purposes only and is not intended to limit the invention in any sense.

As will be apparent to one having skill in the art, the present invention may be advantageously used in a variety of centrifuge devices commonly used to separate blood into its components. In particular, the present invention may be used with any centrifugal apparatus regardless of whether or not the apparatus employs a one-omega/two-omega sealless tubing connection.

It will also be apparent that the teachings of the present invention can also be used for separating particles and blood cells as well as other cells. The description refers to both particles and cells and it is understood that both are used interchangeably without departing from the spirit of the invention.

As embodied herein and illustrated in FIG. 1, the present invention includes a particle separation disposable system 10 for use with a centrifuge rotor 12. Preferably, the centrifuge rotor 12 is coupled to a motor (not shown) via an arm 14, shown in FIG. 2, so that the centrifuge rotor 12 rotates about its axis of rotation A—A.

Figure 2:
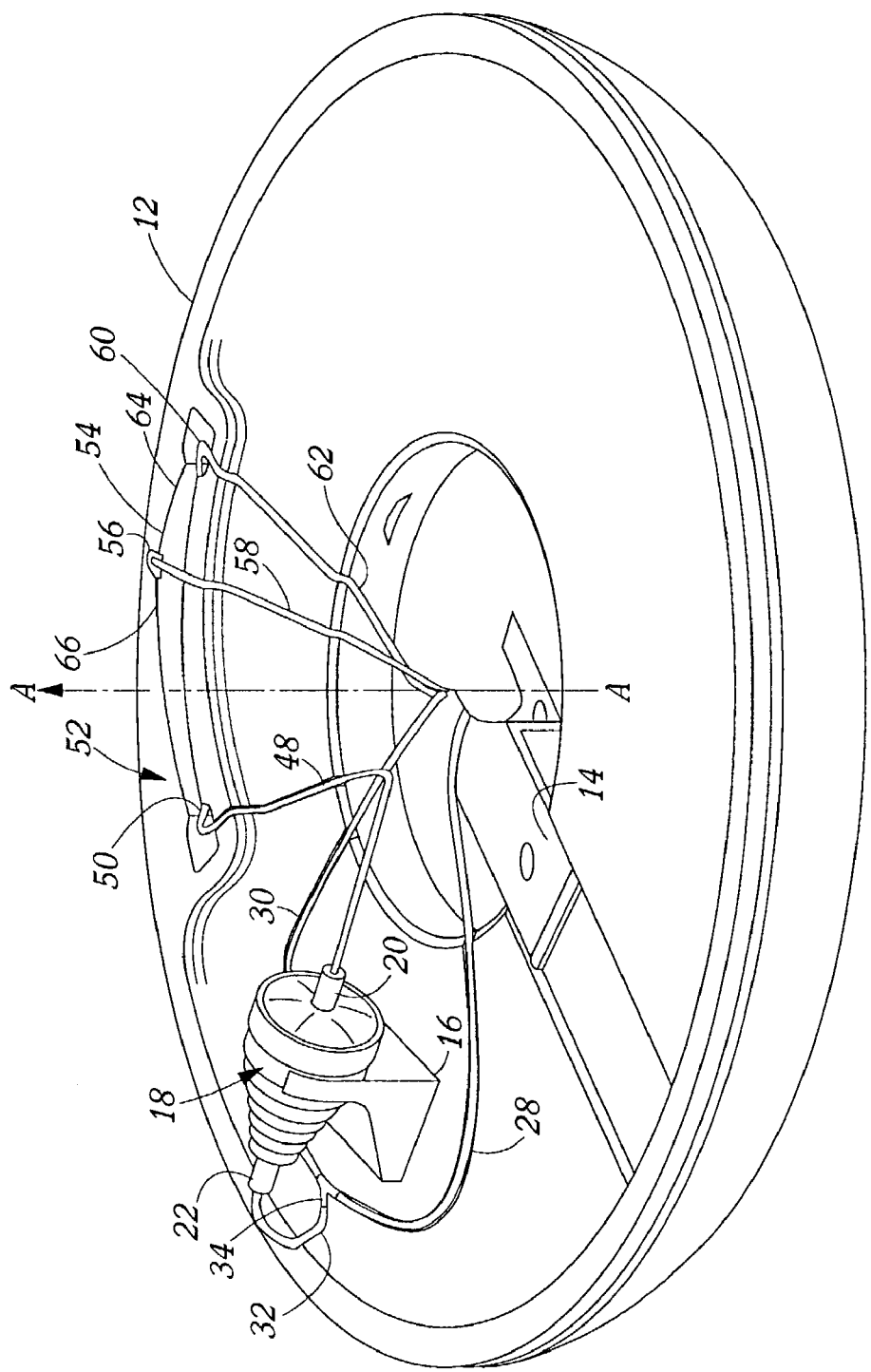
FIG. 2 is a perspective view of a fluid chamber and separation vessel mounted on a centrifuge rotor as depicted in FIG. 1.

As shown in FIG. 2, a holder 16 is provided on a top surface of the rotor 12. The holder 16 releasably holds a fluid chamber 18 on the rotor 12 such that an outlet 20 for components other than red blood cells, hereinafter called the outlet of the fluid chamber 18, is positioned closer to the axis of rotation A—A than the inlet 22 of the fluid chamber 18. The holder 16 preferably orients the fluid chamber 18 on the rotor 12 with a longitudinal axis of the fluid chamber 18 in a plane transverse to the rotor's axis of rotation A—A. In addition, the holder 16 is preferably arranged to hold the fluid chamber 18 on the rotor 12 with the fluid chamber outlet 20 for components other than red blood cells facing the axis of rotation A—A. Although the holder 16 retains the fluid chamber 18 on a top surface of the rotor 12, the fluid chamber 18 may also be secured to the rotor 12 at alternate locations, such as beneath the top surface of the rotor 12. It is also understood that the fluid chamber 18 could be secured by other well known fixative devices or by other methods other than the holder as shown.

Figure 3:
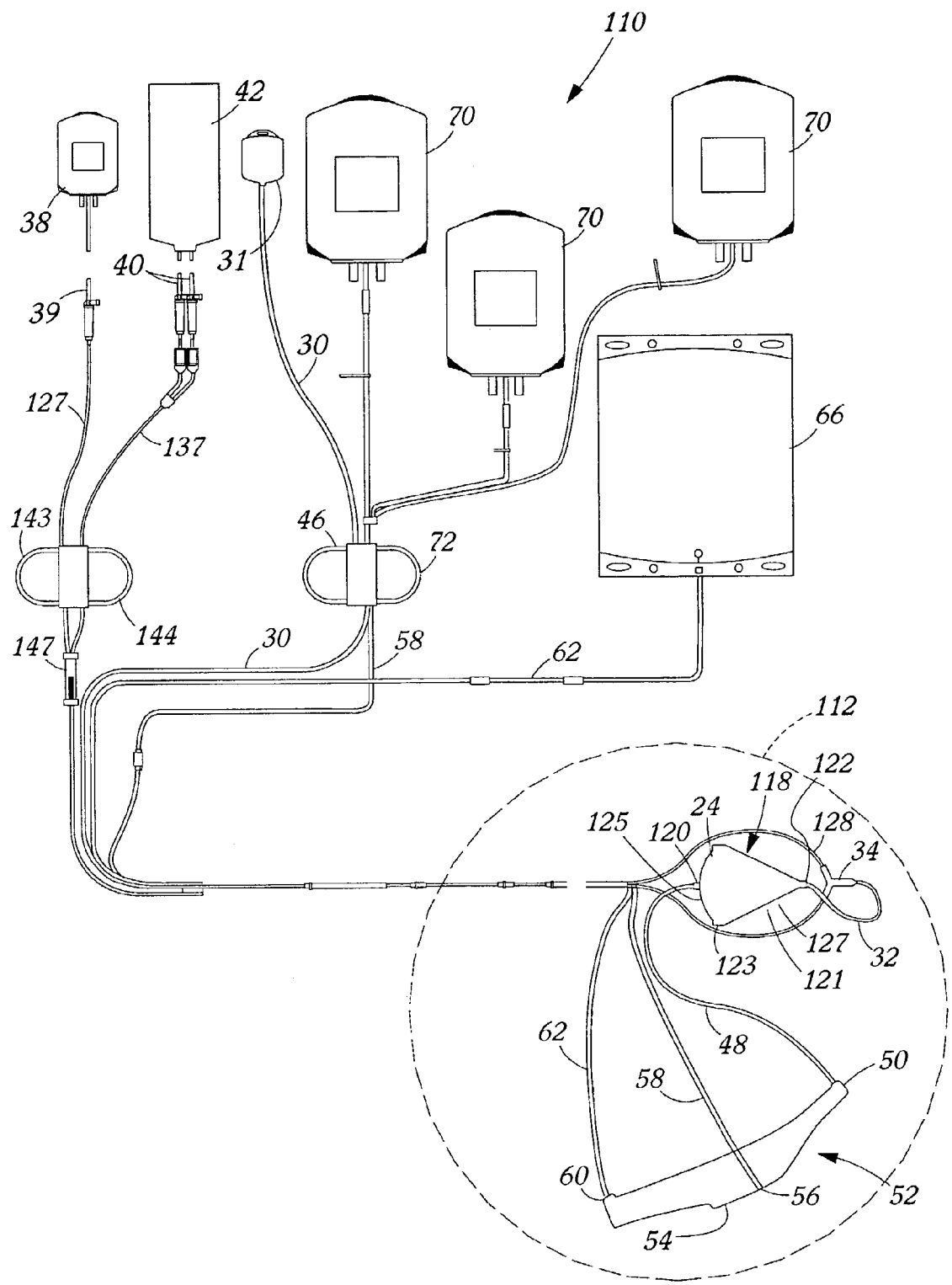
FIG. 3 is a schematic diagram of an alternative particle separation system wherein like numerals as shown in FIG. 1 are used for like elements.
Figure 4:
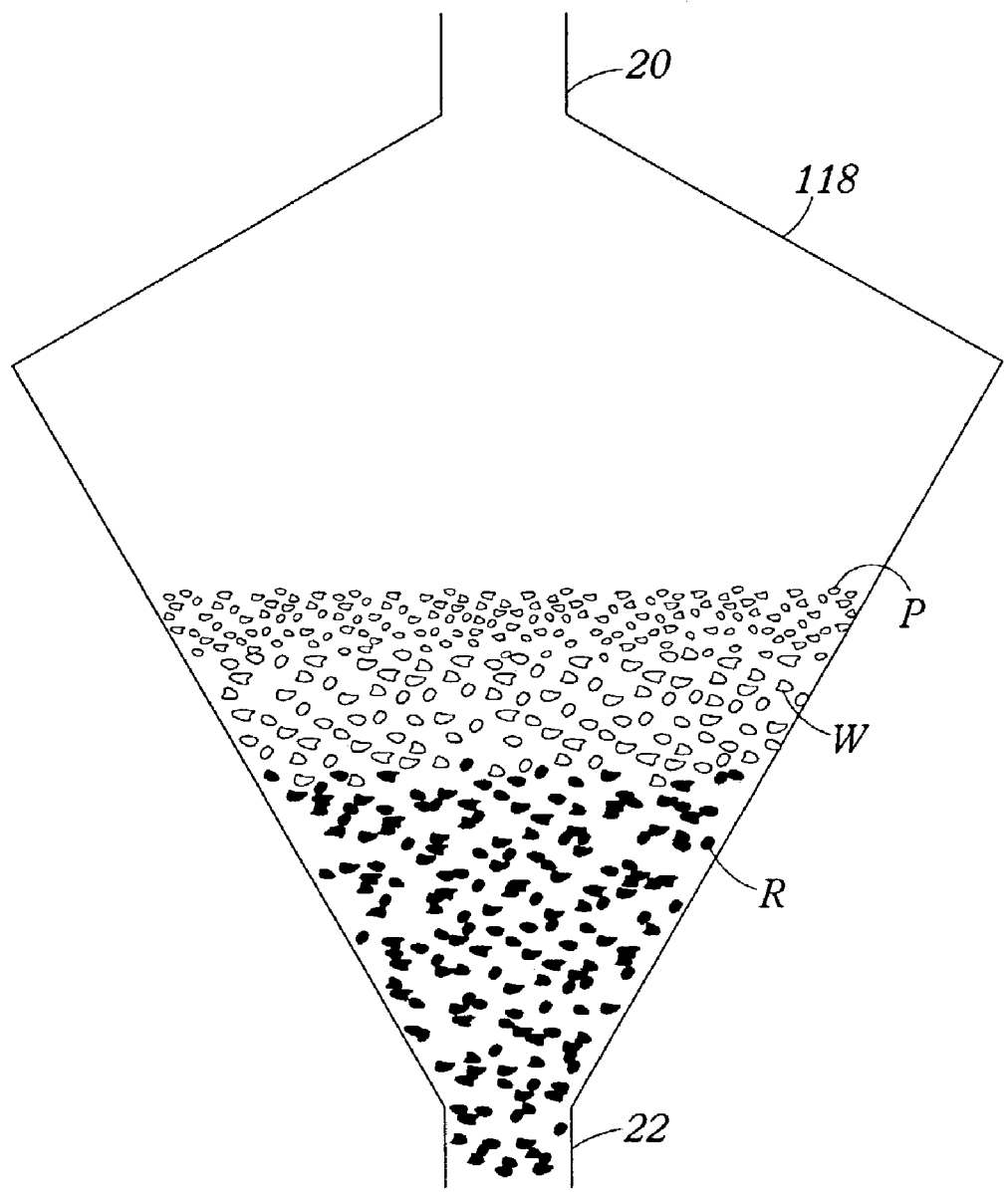
FIG. 4 is a schematic view of sedimented particles in the fluid chamber of FIG. 1 during a red blood cell debulking procedure.

The fluid chamber 18 may be constructed similar to or identical to one of the fluid chambers disclosed in U.S. Pat. No. 5,674,173 referred to above, although in the preferred embodiment the fluid chamber may have smooth sides as shown in FIGS. 3 and 4 and described below. As shown in FIGS. 1 and 2, the inlet 22 and outlet 20 of the fluid chamber 18 are arranged along a longitudinal axis of the fluid chamber 18. A wall 21 of the fluid chamber 18 extends between the inlet 22 and outlet 20 thereby defining inlet 22, the outlet 20, the side and an interior of the fluid chamber 18.

The fluid chamber 18 includes two frustoconical shaped sections 25, 27 joined together at a maximum cross-sectional area 23 of the fluid chamber 18. The interior of the fluid chamber 18 tapers (decreases in cross-section) from the maximum cross-sectional area 23 in opposite directions toward the inlet 22 and the outlet 20. Although the fluid chamber 18 is depicted with two sections (25, 27) having frustoconical interior shapes, the interior of each section may be paraboloidal, or of any other shape having a major cross-sectional area greater than the inlet or outlet area.

The fluid chamber 18 may be constructed from a unitary piece of plastic or from separate pieces joined together using known fixative or sealing methods to form separate sections of the fluid chamber 18. The fluid chamber 18 may be formed of a transparent or translucent copolyester plastic, such as PETG, to allow viewing of the contents within the chamber interior with the aid of an optional strobe (not shown) during a separation or debulking procedure.

As shown in FIG. 1, a groove 24 may optionally be formed on an inner surface of the fluid chamber 18 at a position of the maximum cross-sectional area 23. The groove 24 is defined by top and bottom wall surfaces oriented substantially perpendicular to the longitudinal axis of the fluid chamber 18 and an inner surface of the fluid chamber 18 facing the longitudinal axis. Preferably, the groove 24 is annular, however, the groove 24 may also partially surround the longitudinal axis of the fluid chamber 18.

It is believed the optional groove 24 may help to disperse Coriolis jetting for liquid within the fluid chamber 18. Liquid flowing into the fluid chamber 18 may undergo a Coriolis jetting effect. This jetting flow may cause liquid and particles to pass along an interior wall surface of the fluid chamber 18 and faster sedimenting particles such as the red blood cells described below will mix with the slower sedimentation particles and may be removed from the chamber. The fluid chamber 18 including groove 24 may counteract these effects by channeling Coriolis jetting flow in a circumferential direction partially around the axis of fluid chamber 18. Therefore, the groove 24 may improve the distribution of particles for maximum sedimentation, especially when liquid flow rates increase.

A plurality of steps 26 are optionally formed on an inner surface of the fluid chamber 18 between the maximum cross-section 23 of the chamber 18 and the inlet 22. Each step 26 has a base surface oriented substantially perpendicular to the longitudinal axis of the fluid chamber 18, as well as a side surface positioned orthogonal to the base surface. Although FIG. 1 depicts a corner where the side surface and the base surface intersect, a concave groove may replace this corner. In a one embodiment, each step 26 is annular and surrounds the axis of the chamber 18 completely to bound a cylindrical shaped area. Alternatively, the steps 26 may partially surround the axis of the chamber 18.

The inclusion of steps 26 in the fluid chamber 18, may decrease the flow of faster sedimenting particles from the channel, thus also improving distribution of particles in the chamber for sedimentation. The steps 26 may provide this improvement by providing momentum deflecting and redirecting surfaces to reduce Coriolis jetting in fluid chamber 18. When Coriolis jetting takes place, the liquid and particles of the jet travel along an interior surface of the fluid chamber 18 that faces the direction of centrifuge rotation. Therefore, the jet may transport particles along the fluid chamber interior surface to be removed from the separation chamber with the diluting or sedimentation fluid described below. Steps 26 may direct or alter the momentum of the Coriolis jet flow of liquid and particles generally in a circumferential direction about the axis of the fluid chamber 18, thus enhancing desired mixing with the diluting, elutriation or sedimentation fluid and assuring that the required particles remain in the chamber 18 until they are sedimented.

The inclusion of the groove 24 and steps 26 as described above are optional. The inner surface of the chamber 18 also may be smooth as shown schematically in the preferred embodiment of FIGS. 3 and 4. As further described below, the preferred embodiment does not have the optional steps and groove as absence of such steps and groove may aid in preventing cell capture and adherence.

As shown in FIG. 1, the system 10 which depicts a disposable further includes a first conduit or line 28, second or debulk conduit or line 30, an inlet conduit or line 32 in fluid communication with the inlet 22 of the fluid chamber 18, and a three-way or Y connector 34 having three legs for flow or fluidly connecting the first conduit 28, second or debulk conduit 30, and inlet line 32. The first conduit 28 includes a coupling 36 for flow-connecting the first conduit 28 with conduit or line 27, coupling 39 and a first source 38 containing fluid carrying particles to be separated from one another or the source blood product containing white blood cells. Likewise, the first conduit 28 is connected by coupling 36 to conduit or line 37 which includes couplings 40 for flow-connecting the first conduit 28 with a second source 42 containing a low density diluting, sedimentation or elutriation fluid. The couplings 39 and 40 are preferably any type of common medical coupling devices, such as spikes or sterile tubing connectors.

As shown in FIG. 1, the first conduit 28 includes a first tubing loop 44. During use, the first tubing loop 44 is mounted in a peristaltic pump (not shown) for respectively pumping the fluid to be separated and the diluting, sedimentation or elutriation fluid from the first and second sources 38 and 42, respectively.

The fluid and particles from the first source 38 and the diluting, sedimentation or elutriation fluid from the second source 42 flow through the respective first conduit 28 to the three-way connector 34. These substances then flow through the inlet line 32 into the inlet 22 of the fluid chamber 18. In the fluid chamber 18, turning with rotor 12, the particles in the centrifugal field separate according to differences in sedimentation velocity leaving faster sedimenting particles in the fluid chamber 18 and allowing some slower sedimenting particles to flow from the fluid chamber 18 as will be described below.

As the fluid chamber 18 is loaded with particles as is more fully described below, the fluid and particles having a relatively slower sedimentation velocity, which generally includes plasma, platelets, and possibly some white blood cells, flow through the fluid chamber outlet 20 into conduit tubing or line 48. As shown in FIGS. 1 and 2, the tubing 48 is connected to an inlet 50 of a separation vessel 52 or particle concentrator mounted to the centrifuge rotor 12. As described below, the separation vessel 52 or concentrator separates particles from fluid. Also during any elutriation process to separate the white blood cells into subsets such separated subsets will flow from the fluid chamber 18 to the separation vessel 52 or concentrator as more fully described below.

Adjacent to an outer portion of the centrifuge rotor 12, the separation vessel 52 or concentrator has a collection well 54 for collecting particles flowing into the separation vessel 52 or concentrator. Rotation of centrifuge rotor 12 sediments particles into the collection well 54 while slower sedimenting fluid and possibly some slower sedimenting particles remain above a top boundary of the collection well 54. The collected particles in the collection well 54 can include any cells or particles that have exited the fluid chamber 18, or separated subsets of white blood cells, as noted above.

The collection well 54 has a particle concentrate outlet 56 connected to a particle concentrate line or conduit 58. The particle concentrate line 58 removes particles retained in the collection well 54 along with a small portion of fluid as is more fully described below. The separation vessel 52 also includes a fluid outlet 60 connected to a fluid outlet line or conduit 62. The fluid outlet line 62 removes fluid flowing above a top boundary of the collection well 54. In addition, the fluid outlet line 62 may remove some slower sedimenting particles flowing above the top boundary layer past the collection well 54.

Preferably, fluid outlet 60 is located at or adjacent to one end of the separation vessel 52 or concentrator, and the inlet 50 is located at or adjacent to an opposite end of the separation vessel 52 or concentrator. This spacing ensures ample time for separation of particles from fluid, collection of a substantial number of particles in the collection well 54, and corresponding removal of a substantial number of particles including any separated subsets of white blood cells through the particle concentrate line 58.

In the embodiment shown in FIG. 2, the separation vessel 52 or concentrator is placed in a groove 64 formed in the rotor 12. Preferably, the separation vessel 52 or concentrator is a channel formed of a semi-rigid material so that a valley 66 in an outer wall of the groove 64 forms the collection well 54 when the separation vessel 52 or concentrator expands in response to fluid and particles in the separation vessel 52 or concentrator encountering centrifugal forces. As shown in FIG. 2, the top surface of the rotor 12 preferably includes retainer grooves for receiving the first and second conduits 28 and 30, three-way connector 34, inlet line 32, tubing 48, particle concentrate line 58, and fluid outlet line 62.

As shown in FIG. 1, the fluid outlet line 62 is fluidly coupled to a fluid collection container 66 for collecting fluid removed from the separation vessel 52 or concentrator, and the particle concentrate line 58 is fluidly coupled to one or more particle collection containers 70 for collecting particles removed from the separation vessel 52 or concentrator. Preferably, the particle concentrate line 58 includes a tubing loop 72 capable of being mounted in a peristaltic pump for pumping particles through the particle concentrate line 58. The pump for tubing loop 72 regulates the flow rate and concentration of particles in particle concentrate line 58. The white blood cells of interest will be collected into one of the bags 70. It is understood that any number of bags 70 can be used to collect the desired subsets of white blood cells. FIG. 3, as will be more fully described below, illustrates three collection bags for the blood cells of interest. Platelets can also be collected in a separate bag if desired.

After sedimentation in chamber 18, as is more fully described below, red blood cells are removed through inlet 22 to inlet conduit 32. The debulked red blood cells then pass through Y connector 34 to debulking conduit 30. As shown in FIG. 1, conduit 30 is fluidly coupled to a red blood cell collection container or debulked cell collection container 31 for collecting red blood cells collected during the debulking procedure. Preferably the red blood cell collection or debulk line or conduit 30 includes a tubing loop 46 capable of being mounted in a peristaltic pump for pumping red blood cells through conduit 30.

To control flow rates of substances and rotational speed of the rotor 12 during operation of the system 10, a controller (not shown) controls pumps (not shown) for pumping substances through the tubing loops 44, 46 and 72 and controls a motor (not shown) for rotating the centrifuge rotor 12.

FIG. 3 shows an alternative embodiment of the invention having fluid chamber 118 in the disposable separation system 10. Elements common to the embodiments of FIGS. 1 and 3 have like reference numbers and description of such elements can be found with respect to FIG. 1. FIG. 3 also illustrates an optional third collection bag 70 for the white blood cells of interest. As described above with reference to FIG. 1, any number of collection bags can be used.

The fluid of chamber 118 of FIG. 3 has a wall 121 with a smooth interior side. The wall 121 of the fluid chamber 118 generally forms a conical shape and lacks the steps 26 or groove 24 of the fluid chamber 18 of FIG. 1. Absence of steps and grooves in the wall 121 may permit some Coriolis jetting. However, use of the groove may be disadvantageous in that cells or particles may be captured therein. Also cells or particles may tend to adhere to the steps. Therefore it is believed more beneficial to omit the steps or grooves for maximum cell or particle recovery.

The inlet 122 and outlet 120 of the fluid chamber 118 of FIG. 3 are arranged along a longitudinal axis of the fluid chamber 118. The wall 121 of the fluid chamber 118 extends between the inlet 122 and outlet 120 defining the interior of the fluid chamber.

As with the fluid chamber of FIG. 1 the fluid chamber 118 may be formed of two frustoconical-shaped sections 125, 127 joined together at a maximum cross-sectional area 123 of the fluid chamber 118. The interior of the fluid chamber 118 also tapers from the maximum cross-sectional area 123 in opposite directions toward the inlet 122 and the outlet 120.

Similar to the fluid chamber 18 of FIG. 1, fluid chamber 118 also may optionally be constructed from a unitary piece of plastic or from separate pieces joined together to form separate sections of the fluid chamber 118. The separate pieces may by joined together by any known fixative material or method known in the art. The fluid chamber may be formed of similar material as that described with respect to fluid chamber 18 above.

In FIG. 3 fluid and particles from the first source 38 are connectable by conduit 127 and tubing loop 143 associated with a peristaltic pump to air chamber 147. Also diluting, sedimentation or elutriation fluids from source 42 are connectable by conduit 137 and tubing loop 144 associated with a peristaltic pump to air chamber 147. Air chamber 147 provides an inlet filter for filtering aggregates prior to particle separation. Also the air chamber 147 acts as a bubble trap and an air detection chamber. The air chamber 147 further functions as a fluid pulse suppressor. Use of air chamber 147 is optional, however, and it is also understood that it can be omitted and the source delivery configuration of FIG. 1 can be used.

A preferred method of separating components of blood and, in particular, separating white blood cells from red blood cells is discussed below with reference to FIGS. 1–4. Although the invention is described in connection with a blood component separation process and specifically a white blood cell separation or fractionation process, it should be understood that the invention in its broadest sense is not so limited. The invention may be used to separate a number of different types of particles. It is understood that the method could be used with a disposable separation system 10 or 110 having the fluid chamber 18 of FIG. 1 or the fluid chamber 118 of FIG. 3. Both will be referred to alternatively in the description of the method below. Also, it is understood that either the source and fluid delivery configuration of FIG. 1 or FIG. 3 could also be used.

Initially, blood is collected from a patient and this blood is separated in a centrifugal separation process to isolate what is known as a blood product containing white blood cells. During this initial centrifugation process, platelet rich plasma and a portion of the red blood cells and more dense white blood cells may be separated from the blood, leaving the resulting white blood cell product. In addition, this resulting blood product most likely includes some platelets and red blood cells. Not all starting blood products will require an initial centrifugal separation. For example, collected blood from umbilical cords is generally not subject to an initial centrifugal separation. The starting blood product will then be provided from first source 38 in the apparatus described above.

The initial separation of the collected blood described above is preferably performed on a centrifuge (not shown) separate from the system 10, such as a dual stage or single stage centrifugal separator. In an alternative embodiment, the centrifuge rotor 12 may include structure for providing initial blood component separation on the centrifuge rotor 12, as disclosed in above-referenced U.S. Pat. No. 5,674,173. It is understood that the separated blood product could also be collected and initially separated if desired by other methods.

The resulting separated or collected blood product is placed in the first source 38 shown in FIG. 1, and the first source 38 is coupled to the first conduit 28 through conduit 27, 127. In addition, the second source 42 containing the diluting, sedimentation or elutriation fluid is coupled to the conduit 28 through the conduit 37, 137. The centrifuge rotor 12 is rotated about the axis of rotation A—A, at approximately 2400 rpm. The blood product is pumped from source 38 at a low flow rate and loaded into the fluid chamber 18, 118. The flow of blood product from source 38 is then stopped by a valve or other well-known mechanism. Flow of diluting, sedimentation or elutriation fluid is then started to rinse conduit 28 and/or wash the loaded blood product. The diluting, sedimentation fluid or elutriation fluid passes through conduit 28 and Y connector 34, and inlet conduit 32 into the inlet 22 of chamber 18 or the inlet 122 of chamber 118.

The inlet pump 44 or 144 associated with the tubing loop is stopped to stop the flow of low density diluting, sedimentation or elutriation fluid into the chamber 18, 118. As the centrifuge continues to rotate the particle constituents loaded in the chamber sediment under the resulting centrifugal force. The sedimentation of the particle constituents is shown schematically in FIG. 4 for fluid chamber 118 with the red blood cells R, including red blood cells that have adhered by rouleaux, being shown as sedimenting at the bottom near inlet 22 of the chamber 18. White blood cells W and platelets P are also schematically shown.

After sedimentation of the particle constituents of the blood product, the pump associated with tubing loop 46 is activated to remove or debulk at a low flow rate the sedimented red blood cells R through the inlet 22 of the chamber 18 or the inlet 122 of the chamber 118 and then through inlet conduit 32 and debulking conduit 30 to container 31.

After removal of red blood cells, the white blood cells remaining in chamber 18 or 118 can be separated by elutriation, as described below, or the inlet pump associated with tubing loop 44, 143 can be restarted to reintroduce a second batch of blood product from source 38 into chamber 18, 118.

The elutriating step for separating white blood cells into the desired subsets can be done after each debulking procedure or after the source 38 is empty of blood product. The only requirement is that there be a sufficient number of white blood cells in chamber 18, 118 to achieve effective separation or fractionation. Therefore, the white blood cell content of the starting blood product should be considered in determining the sequence order of the elutriation step.

For collection of fractionated or separated white blood cells or separated desired particles an operator, after debulking or after the first source 38 is empty, slowly increases the inlet pump speed associated with tubing loop 44, 144, decreases the centrifuge speed, or increases the density or viscosity of the diluting, sedimentation or elutriation fluid to separate the cells in chamber 18 into subsets by elutriation, as is well known in the art. Such separated subsets are then concentrated in separation vessel or concentrator 52.

Although the preferred embodiment discloses separating the white blood cells in subsets using elutriation in chambers 18 and 118, it is also understood that a second separate chamber (not shown, but similar to chamber 18, 118) could be fluidly connected between chamber 18, 118 and separation vessel or concentrator 52 wherein the white blood cells can be separated into subsets using the elutriation separation process in the second chamber. Also, the elutriative separation can occur after the white blood cells are collected into a bag 70 as a separate processing step. Furthermore, the white blood cells could also be separated into subsets using the fluidized bed technology of U.S. Pat. No. 5,674,173 after debulking of red blood cells.

The loading, adding of low density fluid, sedimenting, debulking and elutriating steps, (if done after debulking), described above are thus repeated until the entire blood product has been separated or fractionated into desired components or desired subsets and debulked of red blood cells.

In the preferred embodiment the cells loaded in chamber 18, 118 are washed by addition of a low density diluting, sedimentation, or elutriation fluid. It is desirable that such low density fluid contain a protein such as Human Serum Albumin (HSA) or a fluid sedimentation agent such as Hydroxyethyl Starch (HAES). It is preferred that the diluting fluid be selected to encourage the red blood cells to adhere, forming red blood cell rouleaux. As noted above, this is a factor in increasing the red blood cell sedimentation velocity. Increases in such sedimentation velocity assure that the red blood cells will sediment out more completely to be recovered from the inlet 22, 122 of the fluid chamber 18, 118. This permits the red blood cells to be effectively debulked or separated from the chamber 18, 118.

It is understood that the protein and sedimentation agent specified above are only exemplary and that other well known proteins or sedimentation agents could be or could form the diluting, sedimentation fluid. It is also understood that the low density fluid could be media or plasma.

When the present invention is used to separate particles including red blood cells, the red blood cells are encouraged to rouleaux. The use of the diluting low density fluid with protein or the sedimenting fluid enhances the occurrence of red blood cell rouleaux. Adding the above-mentioned fluid to the substances in the fluid chamber 18, 118 encourages such adhesion of red blood cells and also increases their sedimentation velocity as described above. Because rouleaux of the red blood cells is encouraged, the red blood cells sediment out from the white blood cells.

Although the diluting, sedimentation or elutriation fluid is added only at certain parts of the process, it is understood that other configurations are possible. For example, the fluid chamber 18, 118 could be modified to include separate inlets for blood components and diluting or sedimentation fluid. The diluting or sedimentation fluid could also be added to the blood components in the first source 38 before, or at the beginning of, a batch separation process. It is further understood that the selection of elutriation fluid may depend on whether the subsets will be separated by an elutriation technique after debulking.

As the blood product is being loaded into the separation chamber 18, 118, and during the elutriating step, the diluting, sedimentation or elutriation fluid, plasma, platelets, and the white blood cells and any other materials flowing from the fluid chamber outlet 20, 120 pass through the intermediate tubing 48 to the inlet 50 of the separation vessel 52 or concentrator. In the separation vessel 52 or concentrator, centrifugal force caused by rotation of the rotor 12 retain the particles in the collection well 54, while the diluting fluid and plasma flow through the fluid outlet 60 and fluid outlet line 62 to container 66. This separates the platelets and other particles from the diluting fluid and plasma.

The particles and a portion of the fluids flow through the particle concentrate line 58 to one or more particle collection containers 70, and the diluting, sedimentation or elutriation fluid and plasma flow through the fluid collection line 62 to the fluid collection container 66. As described above, any desired number of containers 70 can be used to collect the desired separated subsets of cells, including any separated subsets of white blood cells.

It is understood that although the above procedure is described with respect to debulking red blood cells from white blood cells it also can be used to separate first particles from second particles or to practice cell selection of desired particles.

The instant debulking procedure could achieve effective removal of RBCs without a significant loss of WBCs, and can achieve such in a closed system. The capacity of the system of the instant invention can be increased by placing several small chambers in parallel or series, or by using one large chamber. Ideally, the combined chamber volume should be capable of debulking approximately 15 to 45 ml of RBC in one hour, and elutriating (in one or two cycles) approximately $2 \times 10^{10}$ WBC in two hours. It is anticipated that the fluid chambers 18 and 118 can be sized to contain any desired amount of product though capacity to contain 40 ml of product is preferred.

Alternatively, one (or more) large chambers with a volume of approximately 40 mL could be used. The current disposable could easily be adapted to accommodate this large a chamber, provided the chamber could be recessed in the rotor 12.

The disposable particle separation system may also optimally include sensors at various output locations such as in the particle concentrate line for monitoring the types of cells and concentration being collected. Any known type of a sensor could be used.

EXAMPLES

The effectiveness of red blood cell debulking to achieve a purified or fractionated white blood cell product was evaluated in various experiments. The debulking protocol used in the experiments reported is as follows:

1. Obtain the residuals from an apheresis procedure, separate and collect the white blood cells (WBC) by centrifugation, and adjust the hematocrit to 5–20%.
2. Obtain a pre-product sample of this product, label it PRE, and analyze the sample (in triplicate) using a Coulter Automated Cell Counter available from Coulter Corporation, Miami, Fla.
3. Calculate the volume of product required to achieve a cell load inside a separation chamber of 3.51 mL.
4. Transfer the appropriate volume of product to a 150 mL transfer pack.
5. Prepare diluent containing Human Serum Albumin or Hydroxyethyl Starch, transfer 50 mL to a 150 mL transfer pack, and the remainder to a second transfer pack.
6. Prepare a tubing disposable set consisting of an inlet pump loop, a debulking pump loop (with 0.044" ID tubing), an outlet line, and a separation chamber. These elements correspond to the pump loop 44, the red blood cells loop 46, the inlet line 28, an outlet line for the debulked red blood cells 30, and the chamber 18 of FIG. 1.
7. Attach the outlet of the debulking pump to a fraction collector, set-up to collect 400–500 μL fractions in 5 mL polypropylene test tubes.
8. Attach the outlet line, from the outlet of the separation chamber, to a 600 mL transfer pack labeled OUTLET.
9. Prime the tubing set with prepared diluent.
10. Load the cell product into the separation chamber at a flow rate of 4 mL/min and a centrifuge speed of 2400 rpm.

11. While cells are being loaded into the separation chamber, collect the fluid and cells exiting through the chamber outlet in a transfer pack.
12. Rinse the tubing and the cells inside the separation chamber with 50 mL of diluent.
13. Stop the inlet pump, and allow the cells inside the separation chamber to sediment for a previously defined length of time.

the 1% value is arbitrary and extremely low (compared to other preliminary processing procedures) it provides a means of comparing results obtained under different debulking conditions.

Some of the conditions that were evaluated as part of this feasibility study are provided in Table 1. The results of each reported experiment using the set up and analyzer described above are expressed in terms of RBC removal, as described previously.

TABLE 1

| | RUN CONDITIONS | | | | | | RBC REMOVAL (%) | | | FINAL RBC:WBC | | |
|---|---|---|---|---|---|---|---|---|---|---|---|---|
| Run | HCT Load (%) | RBC Load (mL) | WBC Load (#) | Initial RBC: WBC | Diluent | Time (min) | Lymph Loss (1%) | Mono Loss (1%) | WBC Loss (1%) | Lymph Loss (1%) | Mono Loss (1%) | WBC Loss (1%) |
| 1 | 9.0 | 2.23 | 1.29E+09 | 19.1:1 | 5% HSA | 5 | 61.9 | 53.3 | 54.0 | 7.4:1 | 9.0:1 | 8.9:1 |
| 2 | 9.0 | 2.55 | 1.20E+09 | 23.6:1 | 5% HSA | 15 | 71.3 | 66.0 | 71.7 | 6.8:1 | 8.1:1 | 6.7:1 |
| 3 | 10.3 | 2.52 | 1.53E+09 | 18.3:1 | 5% HSA | 10 | 52.9 | 52.4 | 53.0 | 8.7:1 | 8.8:1 | 8.7:1 |
| 4 | 9.5 | 1.97 | 1.42E+09 | 15.4:1 | 5% HSA | 4 | 55.4 | 26.3 | 55.4 | 6.9:1 | 11.4:1 | 6.9:1 |
| 5 | 9.3 | 3.33 | 3.61E+08 | 102.4:1 | 5% HSA | 3 | 40.4 | 10.7 | 35.4 | 61.8:1 | 91.7:1 | 66.8:1 |
| 6 | 8.8 | 2.67 | 1.30E+09 | 22.8:1 | 5% HSA | 2 | 50.0 | 17.1 | 50.0 | 11.5:1 | 18.9:1 | 11.5:1 |
| 7 | 9.5 | 2.67 | 1.07E+09 | 27.6:1 | 5% HSA | 1 | 18.9 | 10.2 | 16.2 | 22.6:1 | 24.9:1 | 23.4:1 |
| 8 | 11.4 | 2.48 | 6.19E+08 | 44.5:1 | 0.44% HAES | 5 | 27.9 | 14.3 | 20.6 | 32.6:1 | 38.5:1 | 35.7:1 |
| 9 | 10.7 | 3.28 | 8.20E+08 | 44.5:1 | 0.88% HAES | 5 | 56.6 | 20.8 | 48.7 | 19.6:1 | 35.3:1 | 23.1:1 |

14. Remove cells from the bottom of the separation chamber using the debulking pump and a flow rate of 1 mL/min, and collect cells in small aliquots, using the fraction collector.
15. Discontinue fraction collection once all cells have been removed from the separation chamber.
16. Record the weight of fluid and cells in the transfer pack labeled OUTLET, and in the test tubes.
17. Analyze PRE and OUTLET samples, as well as all test tube aliquots, using a CELL-DYN 4000 System.

The results of the nine experiments are reported in Table 1, below.

In the experiments, the fractions were analyzed using a CELL-DYN 4000 System, manufactured by Abbott Diagnostics Division, Abbott Park, Ill., which uses flow cytometry and absorption spectrophotometry to count, size and classify blood cells and platelets. The reason for selecting the CELL-DYN analyzer is that it has the capability to do five part white cell differentials (Neutrophils, Lymphocytes, Monocytes, Eosinophils, and Basophils), allowing information to be obtained on the sedimentation of white cell sub-sets, along with that of red blood cells.

Following each debulking experiment, cell counts and sample weights were used to calculate the recovery of various cell types as a function of the cumulative volume removed from the separation chamber.

In the examples, the cells removed initially from the bottom of the separation chamber are primarily red blood cells. After removing about 3 mL of cell suspension, however, the fractions contain a mixture of red and white cells. Further, there is some indication that the cells in these later fractions have sedimented according to differences in density (Neutrophils, Lymphocytes, Monocytes, and then Platelets).

The cumulative cell recovery results were then used to calculate the red blood cell recovery at the point in which there was a measurable recovery of Lymphocytes or Monocytes (1%). A 1% recovery of Lymphocytes or Monocytes in the debulked red cells corresponds to a 1% loss of either cell type for additional processing (such as elutriation). Although As indicated in Table 1, Experiments or Runs 1 through 9 were conducted using a starting product with a hematocrit of approximately 10%. This hematocrit was selected on the basis of the desire to load the chamber with a cell volume of 3.51 mL, consisting of cells from only one apheresis procedure (which provides only minimal levels of WBC), and the need to ensure rouleaux formation. It is believed that at hematocrits below approximately 2%, the "red cell sedimentation velocity is equal to the white cell sedimentation velocity", suggesting that red cell rouleaux is small or non-existent. This starting hematocrit was also selected to better simulate a realistic purification process.

The WBC load in the chamber in Experiments 1 through 9 varied from $3.6 \times 10^8$ to $1.5 \times 10^9$, but because of the 10% hematocrit, the ratio of RBC to WBC in the cell load was always well above 10:1 (range 15:1 to 102:1). It is believed that ratio should be less than 10:1 to prevent red cells from interfering with cell separation by elutriation, and if not less than 10:1 then the starting product should undergo a processing procedure such as the RBC debulking procedure described. Data on the initial ratio of RBC to WBC, and final ratio in the separation chamber following removal of 1% Lymphocytes, 1% Monocytes, or 1% total WBC is provided in Table 1.

After the starting products were loaded into the chamber, the tubing and cells inside the chamber were washed with a diluent. In Experiments or Runs 1 through 7 the diluent consisted of 5% Human Serum Albumin in Isolyte S (or simply 5% HSA). It is believed rouleaux formation only occurs in the presence of protein at a concentration of at least 1–2 g %. Therefore, 5% albumin was believed to be sufficient.

In Experiments or Runs 8 and 9, diluents containing a sedimenting agent (hydroxyethyl starch) were used in place of the protein containing diluents. The 0.44% HAES diluent actually consisted of 0.44 g % Hydroxyethyl Starch and 0.20 g % Trisodium Citrate, in Isolyte S, pH 6.93. This concentration of HAES was derived from information provided in the *Spectra Operator's Manual* for the Spectra Apheresis System, which recommends that a hydroxyethyl starch solution be used in place of standard ACD-A in certain WBC procedures, and that this solution be administered at an Inlet to AC ratio of approximately 13:1. The level of HAES was doubled in Experiment 9, to 0.88% HAES, to check for a dose response. The 0.88% HAES diluent increased the RBC removal attainable with a 1% loss of Lymphocytes from 28 to 57%, and increased the RBC removal from 14 to 21% with a 1% loss of Monocytes. Higher levels of HAES can also be used for red blood cell debulking (especially for Monocyte applications). Alternatively, some combination of protein and HAES (at a lower level) can be used.

Figure 5:
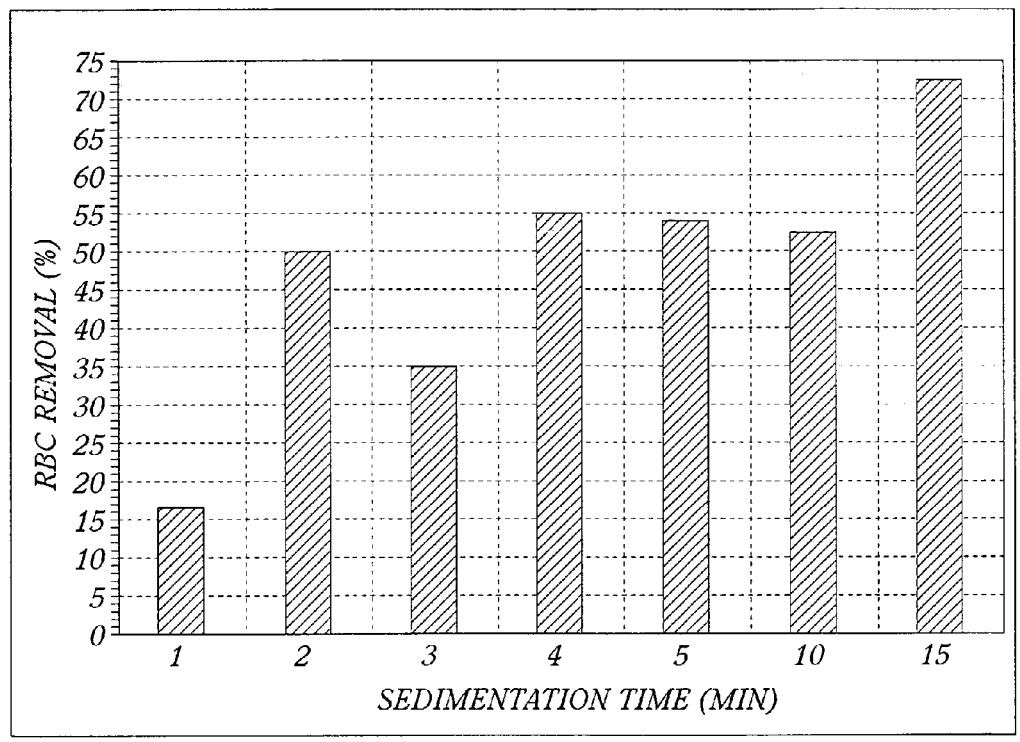
FIG. 5 depicts sedimentation time versus red blood cell removal for examples in accordance with the instant invention.

The other condition evaluated during these experiments was sedimentation time. As illustrated in FIG. 5, red blood cell (RBC) removal increased as the sedimentation time was increased from 1 to 15 minutes. These results suggest that it is preferred to allow red blood cells to sediment in the chamber for at least 5 minutes.

During each debulking experiment, starting cell products (with a total cell volume of approximately 3.51 mL) were loaded into the chamber at a flow rate of 4 mL/min and at a centrifuge speed of 2400 rpm. These conditions caused the cell mass in the chamber to reach the major diameter. During the process of loading and washing the cell mass with diluent, fluid and some cells exited through the chamber outlet. This product (called OUTLET) was collected and later analyzed to determine the level of platelet removal attained prior to RBC debulking. The platelet removal, and WBC removal (or WBC loss), results are provided in Table 2.

TABLE 2

| RUN CONDITIONS | | | CELL REMOVAL | |
|---|---|---|---|---|
| RUN (#) | CELL LOAD (mL) | PLT LOAD (#) | DILUENT | PLT (%) | WBC (%) |
| 1 | 3.41 | 2.38E+10 | 5% HSA | 40.7 | 0.1 |
| 2 | 3.39 | 2.88E+10 | 5% HSA | 49.9 | 0.0 |
| 3 | 3.38 | 2.40E+10 | 5% HSA | 48.4 | 0.0 |
| 4 | 3.42 | 5.57E+10 | 5% HSA | 78.8 | 0.1 |
| 5 | 3.56 | 2.40E+10 | 5% HSA | 99.2 | 0.1 |
| 6 | 3.69 | 2.64E+10 | 5% HSA | 69.0 | 0.0 |
| 7 | 3.62 | 3.40E+10 | 5% HSA | 65.5 | 0.3 |
| 8 | 3.19 | 2.43E+10 | 0.44% HAES | 80.5 | 0.5 |
| 9 | 3.57 | 3.22E+10 | 0.88% HAES | 66.6 | 0.1 |

These results indicate that a significant level of platelets (60.0±21.1%) are removed from a starting cell product during the process of loading the separation chamber with a cell volume of approximately 3.51 mL and at an inlet flow rate of only 4 mL/min. The low level of WBC loss associated with this process (0.4±0.6%), suggests that the inlet flow rate can be increased slightly to further increase the level of platelet removal.

The results of the RBC debulking experiments conducted to date suggest that approximately 55% of the red blood cells in a cell product can be removed without significant loss of blood cells using the instant invention. Also, these results indicate that while loading a cell product using the system of the instant invention, the level of contaminating platelets can be reduced by approximately 60%.

It will be apparent to those skilled in the art that various modifications and variations can be made to the structure and methodology of the present invention without departing from the scope or spirit of the invention. For example, the present invention could be used to separate tumor cells from red blood cells, and the cell suspension in the first source 38 may include T cells and/or stem cells. In view of the foregoing, it is intended that the present invention cover modifications and variations of this invention provided they fall within the scope of the following claims and their equivalents.

What is claimed is:

1. A method of debulking red blood cells from white blood cells comprising
    rotating a fluid chamber (18, 118)
    loading the fluid chamber (18, 118) through its inlet (22, 122) with a blood product containing at least white blood cells and red blood cells;
    adding a low density fluid to the loaded blood product to encourage rouleaux of the red blood cells and to increase their sedimentation velocity;
    sedimenting the red blood cells from the white blood cells in the rotating fluid chamber (18, 118) under a centrifugal force; and
    removing the sedimented red blood cells from the white blood cells during the rotating step from the rotating fluid chamber (18, 118) through the fluid chamber inlet (22, 122);
    wherein the fluid comprises Hydroxyethyl Starch.

2. The method of separating first and second particles by sedimentation comprising
    providing a fluid from a source (38) wherein said fluid contains the first and second particles:
    mounting a fluid chamber (18, 118) on a centrifuge rotor (12, 112) for rotation;
    loading the fluid from the source into the fluid chamber (18, 118) through its inlet;
    rotating the fluid chamber (18, 118);
    adding a low density fluid to increase the sedimentation velocity of the particles;
    sedimenting the first and second particles in the rotating fluid chamber (18, 118); and
    removing the particles having the increased sedimentation velocity through the rotating fluid chamber inlet (22, 122);
    wherein the fluid is Hydroxyethyl Starch.

3. A system (10, 110) for debulking first particles from second particles in a blood product comprising
    a source of fluid having at least first and second particles;
    a low density fluid source (42);
    a fluid chamber (18, 118) having an inlet (22, 122) and adapted to be mounted on a rotor (12, 112) for rotation;
    a first conduit (28, 128) fluidly connecting the fluid source (38) having particles and the low density fluid source (42) to the inlet (22, 122) of the fluid chamber (18, 118);
    a debulking conduit (30) fluidly connected to the inlet (22, 122) of the fluid chamber (18, 118) for receiving first particles debulked from the fluid chamber inlet (22, 122) when the fluid chamber (18, 118) is mounted on the rotor (12, 112) for rotation;
    a debulking container (31) connected to the debulking conduit (30) for receiving the debulked first particles; and
    an outlet (20, 120) arranged along a longitudinal axis of the fluid chamber (18, 118) on the opposite end of the fluid chamber (18, 118) from the inlet (22, 122).

4. The system of claim 3 further comprising
    a particle concentrate line (58) fluidly connected to the outlet (20, 120) of the fluid chamber (18, 118); and
    a particle collection container (70) fluidly connected to the particle concentrate line (58) to collect particles flowing through the outlet (20, 120) of the fluid chamber (18, 118).

5. The system of claim 4 further comprising
a fluid outlet line (62) fluidly connected to the outlet (20, 120) of the fluid chamber (18, 118); and
a fluid collection container (70) fluidly connected to the fluid outlet line (62) to collect fluid flowing from the outlet (20, 120) of the fluid chamber (18, 118).

6. The system of claim 5 further comprising
a separation vessel (52) fluidly connected to the outlet (20, 120) of the fluid chamber (18, 118) and the particle concentrate line (58) and the fluid outlet line (62) to separate particles for collection from fluid flowing through the fluid chamber outlet (20, 120).

7. A disposable particle separation system (10, 110) comprising
a first coupling (39) adapted to be connected to a source of particles (38) to be separated;
a second coupling (40) adapted to be connected to a source of low density fluid (42);
a first conduit (28, 128) fluidly connected to the first and second couplings (39, 40);
a fluid chamber (18, 118) fluidly connected to the first conduit (28, 128), wherein the fluid chamber (18, 118) further comprises
an inlet (22, 122);
an outlet (20, 120);
a wall (121) having a smooth interior surface extending between the inlet (22, 122) and outlet (20, 120);
a maximum cross-sectional area (23, 123) in the wall wherein the wall tapers from the maximum cross-sectional area to the inlet (22, 122) and from the maximum cross-sectional area to the outlet (20, 120);
a particle concentrator (52) fluidly connected to the outlet (20, 120) of the fluid chamber (18, 118);
a debulking conduit (30) for receiving particles fluidly connected to the inlet (22, 122) of the fluid chamber (18, 118);
a three-way connector (34) for fluidly connecting the first conduit (28, 128) to the inlet (22, 122) of the fluid chamber (18, 118) and for fluidly connecting the debulking conduit (30) to the inlet (22, 122) of the fluid chamber (18, 118);
an inlet conduit (32) connected to the inlet (22, 122) of the fluid chamber (18, 118) and to the three-way connector (34); and
a debulking collection container (31) fluidly connected to the debulking conduit (30).

8. The disposable particle separation system of claim 7 further comprising
a fluid collection container (66) fluidly connected to the particle concentrator (52); and
a particle collection container (70) fluidly connected to the particle concentrator (52).

9. The disposable particle separation system of claim 7 wherein the particles to be separated include white blood cells to be separated into white blood cell subsets.

10. The disposable particle separation system of claim 7 wherein the debulked particles include red blood cells.

11. A method of separating a white blood cell product having white blood cells and red blood cells into white blood cell subsets comprising
rotating a fluid chamber (18, 118) about an axis of rotation A—A;
loading the fluid chamber (18, 118) through its inlet (22, 122) with the white blood cell product;
adding a low density fluid to the loaded white blood cell product;
sedimenting the white blood cells and the red blood cells in the white blood cell product in the rotating fluid chamber (18, 118);
removing the sedimented red blood cells through the inlet (22, 122) of the rotating fluid chamber (18) to separate the red blood cells from the white blood cells; and
collecting the separated white blood cells;
the method further comprising separating by elutriation the white blood cells into white blood subsets after the removing step.

12. The method of claim 11 further comprising
adding additional low density fluid to the fluid chamber (18, 118) during the separating step.

13. The method of claim 11 further comprising
removing the separated white blood cell subsets through the outlet (20, 120) of the fluid chamber (18, 118);
providing the removed separated white blood cell subsets to a particle concentrator (52);
separating in the particle concentrator (52) fluid from the white blood cell subsets; and
collecting the desired white blood cell subset.

* * * * *